United States Patent

Kalopissis et al.

[11] 4,054,147
[45] Oct. 18, 1977

[54] 4,4-DISUBSTITUTED DIPHENYLAMINES IN DYE COMPOSITIONS FOR KERATINIC FIBERS

[75] Inventors: Grégoire Kalopissis, Neuilly-sur-Seine; Andrée Bugaut, Boulogne-sur-Seine; Françoise Estradier, Paris, all of France

[73] Assignee: L'Oreal, Paris, France

[21] Appl. No.: 551,662

[22] Filed: Feb. 21, 1975

[30] Foreign Application Priority Data

Feb. 22, 1974 Luxembourg .................... 69456

[51] Int. Cl.² ................................ A61K 7/13
[52] U.S. Cl. ................................ 132/7; 8/10; 8/10.1; 8/11; 8/32; 8/10.2; 260/556 A; 260/558 R; 260/562 H; 260/562 P; 260/570.5 P; 260/570.5 S; 260/573; 260/574; 424/DIG. 1; 424/DIG. 2; 424/71
[58] Field of Search ............ 8/10.2, 10, 10.1, 11, 8/32; 260/558 R, 556 A, 562 H, 562 P, 570.5 P, 570.5 S, 573, 574; 132/7

[56] References Cited

U.S. PATENT DOCUMENTS

| 3,200,040 | 8/1965 | Lange | 8/10.2 |
| 3,214,472 | 10/1965 | Charle et al. | 8/10.2 X |
| 3,415,608 | 12/1968 | Tucker | 8/10.2 |

FOREIGN PATENT DOCUMENTS

| 149,676 | 4/1903 | Germany | 8/10.2 |
| 209,121 | 4/1918 | Germany | 8/10.2 |

Primary Examiner—Jerome D. Goldberg
Assistant Examiner—Vera C. Clarke
Attorney, Agent, or Firm—Cushman, Darby & Cushman

[57] ABSTRACT

Diphenylamine of the formula

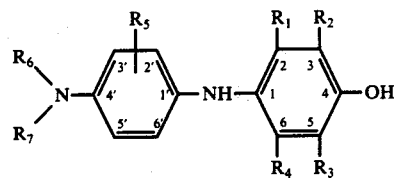

wherein
$R_1$ and $R_4$ each independently represent a member selected from the group consisting of hydrogen, halogen, lower alkyl, lower alkoxy, amino, lower alkyl amino, acylamino, lower carbamylalkyl amino, lower hydroxyalkyl amino, lower carbalkoxy amino and ureido;
$R_2$ and $R_3$ each independently represent a member selected from the group consisting of hydrogen, halogen, lower alkyl, lower alkoxy, acylamino and ureido;
$R_5$ represents a member selected from the group consisting of hydrogen, halogen, lower alkyl and lower alkoxy;
$R_6$ represents a member selected from the group consisting of lower hydroxyalkyl, lower amino alkyl, lower acylamino alkyl, lower mesylamino alkyl, lower carbamylalkyl, lower sulfoalkyl, lower piperidinoalkyl, lower morpholinoalkyl, lower mono alkyl lower amino alkyl and lower dialkyl lower amino alkyl; and
$R_7$ represents a member selected from the group consisting of lower alkyl, lower hydroxyalkyl, lower aminoalkyl, lower acylamino alkyl, lower mesylamino alkyl, lower carbamyl alkyl, lower sulfoalkyl, lower piperidinoalkyl, lower morpholinoalkyl, lower monoalkyl lower amino alkyl and lower dialkyl lower amino alkyl, each of said alkyl and alkoxy moieties containing 1-6 carbon atoms and each of said acyl moieties representing R-CO- wherein R is selected from the group consisting of an aliphatic and aromatic group.

The said diphenylamine is usefully employed in a dye composition for dyeing keratinic fibers.

19 Claims, No Drawings

4,4-DISUBSTITUTED DIPHENYLAMINES IN DYE COMPOSITIONS FOR KERATINIC FIBERS

The present invention relates to diphenylamines or N,N-leuco-indoanilines disubstituted in the 4' position, to their preparation and to compositions for application to keratinic fibers, especially living human hair, to dye or color the same.

A currently utilized technique for dyeing keratinic fibers, and especially living human hair, comprises applying to the hair, in the presence of an oxidizing agent added at the moment of use (generally hydrogen peroxide), a dye composition comprising a mixture in an appropriate cosmetic support, of compounds belonging to one or the other of the two following classes.

The first class of compounds, generally called "oxidation bases" is principally constituted by paraphenylenediamines or paraaminophenols which on oxidation produce para benzoquinonediimines or parabenzoquinonemonoimines.

The second class of compounds, generally called "couplers" include, especially, metaaminophenols, metaacetylaminophenols, metadiamines and metadiphenols. They are compounds with which the benzoquinone mono- or di-imines will react to produce dyestuffs called depending upon their structure, indophenols, indoanilines or indamines.

These dyestuffs, which provide a range of shades of exceptional richness, are primarily characterized by the luminosity and the richness in glints of dyeings or coloration they impart to the fibers dyed therewith.

However, when a complex dyeing composition is employed, i.e. a composition which includes several bases and several couplers, it is very difficult to foresee in the final shade the contribution of each possible couple of oxidation base and coupler. In other words, on the one hand, it is very difficult at the outset to predict with any exactitude, the final shade that will be attained and, on the other hand, for a given dye composition, it is not often easy to be assured of a perfectly reproducible result. These difficulties are increased by the fact that different secondary reactions can modify the final shade, such secondary reactions including, for instance, Bandrowsky base type compounds from the oxidation bases; recondensation of a molecule of an oxidation base on certain indophenols or on certain indoanilines or indamines; and formation of quinones and the like.

Heretofore, it has also been proposed to use in the dyeing of hair some indoanilines which are well defined compounds and which impart to the hair essentially perfectly reproducible shades.

However, some inconvenience has been experienced in the use of these compounds since they possess only a slight affinity for keratinic fibers under conventional conditions for dyeing hair.

The present invention relates to leuco derivatives of indoanilines which are colorless compounds and which, when applied in an aqueous solution to fibers to be dyed, are oxidized at the interior of the keratinic fibers so as to give the corresponding indoanilines. These resulting indoanilines are the colored compounds which are directly responsible for the dyeing of the fibers. The colorations thus obtained exhibit fastness and intensity of coloration which are greater than those of dyeings effected by the direct application of indoanilines, because of the enhanced solubility and better keratinic fiber penetration characteristics of the compounds of the present invention.

The oxidation of leuco derivatives of the present invention to indoanilines can be effected by the oxygen in air or by the use of an oxidizing agent incorporated into the dye composition at the moment of use. Representative oxidizing agents include hydrogen peroxide, urea peroxide and ammonium persulfate.

While the use of leuco derivatives of indoanilines for dyeing hair has already been proposed, the present invention enlarges the family of such leuco derivatives. Thus the leuco derivatives of indoanilines or diphenylamines of the present invention have the formula

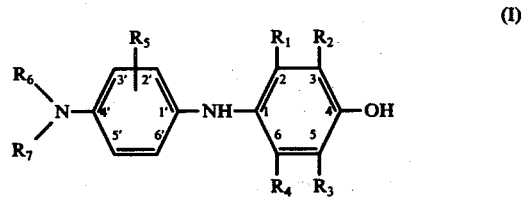

(I)

wherein $R_1$ and $R_4$ each independently represent a member selected from the group consisting of hydrogen, halogen, lower alkyl, lower alkoxy, amino, lower alkyl amino, acylamino, lower carbamylalkyl amino, lower hydroxyalkyl amino, lower carbalkoxy amino and ureido;

$R_2$ and $R_3$ each independently represent a member selected from the group consisting of hydrogen, halogen, lower alkyl, lower alkoxy, acylamino and ureido;

$R_5$ represents a member selected from the group consisting of hydrogen, halogen, lower alkyl and lower alkoxy;

$R_6$ represents a member selected from the group consisting of lower hydroxyalkyl, lower aminoalkyl, lower acylamino alkyl, lower mesylamino alkyl, lower carbamyl alkyl, lower sulfoalkyl, lower piperidinoalkyl, lower morpholinoalkyl, lower mono alkyl lower amino alkyl and lower dialkyl lower amino alkyl; and $R_7$ represents a member selected from the group consisting of lower alkyl, lower hydroxyalkyl, lower aminoalkyl, lower acylamino alkyl, lower mesylamino alkyl, lower carbamyl alkyl, lower sulfoalkyl, lower piperidinoalkyl, lower morpholinoalkyl, lower monoalkyl lower amino alkyl and lower dialkyl lower amino alkyl.

The above lower alkyl and lower alkoxy groups contain from 1 to 6 and preferably 1 to 4 carbon atoms and the acyl group represents R—CO— wherein R is an aliphatic or aromatic radical and represents preferably lower alkyl having 1-6 carbon atoms or phenyl.

The present invention also relates to diphenylamines of formula (I) in the form of their salts, such as, for instances, the hydrochlorides, hydrobromides, sulfates and phosphates thereof.

The diphenylamines of formula (I) are the leuco derivatives of indoanilines of the formula (II)

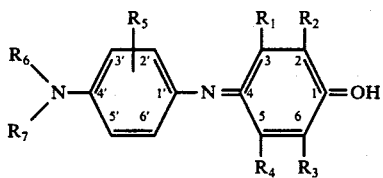

(II)

wherein $R_1$ to $R_7$ have the meanings given above, the said diphenylamines being prepared by reduction of the latter.

These starting indoanilines can be prepared by the condensation of a substituted aniline of the formula

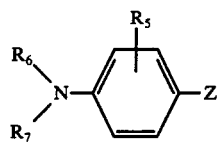

(III)

wherein

Z represents a member selected from the group consisting of $NH_2$ or NO, and $R_5$, $R_6$ and $R_7$ have the meanings given above, or a salt thereof on a substituted phenolic compound of the formula

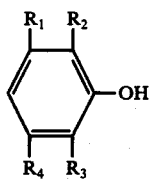

(IV)

wherein $R_1$ to $R_4$ have the meanings given above, or a salt of such a phenolic compound.

When Z represents $-NH_2$, the condensation is carried out in an aqueous or hydroalcoholic or hydroacetonic medium, at an alkaline pH generally greater than 8, in the presence of an oxidizing agent, such as, for example, ammonium persulfate, potassium ferricyanide, hydrogen peroxide, and at a temperature generally between about 0° to 25° C. The alkaline pH can be attained by adding to the reaction medium ammonia or an akaline carbonate, such as sodium carbonate. The molar ratio of substituted phenol to substituted aniline can be between about 1:0.5 to 1:1.2 and preferably between about 1:1 to 1:1.1. The molar ratio of oxidizing agent to phenol is between about 1:1 and 4:1 and preferably between about 1:1 to 2.2:1, when there is used, as the oxidizing agent, ammonium persulfate. This ratio is about 8:1 when hydrogen peroxide is used as the oxidizing agent. Generally, hydrogen peroxide is employed in the form of a 6 weight percent solution. As the reaction medium there can be used water or a lower alkanol preferably ethanol or isopropanol or an acetone-water mixture, or a lower alkanol-water mixture. Generally when an acetone-water or lower alkanol-water mixture is used the ratio of acetone or lower alkanol to water ranges from about 1:3 to 2.25:1. The pH of the reaction medium is alkalinized to pH 8, preferably by the addition thereto of ammonia or a soluble alkaline carbonate.

When Z represents —NO, the condensation is carried out generally at a temperature of about 30° to 60° C and preferably 40° to 55° C, in a water-ethanol mixture, preferably 1:1, which is neutral or has been rendered alkaline by the addition thereto of a dilute sodium hydroxide solution, and in the absence of an oxidizing agent.

The reduction of indoanilines (benzoquinoneimines) of formula (II) is carried out preferably with the aid of an alkaline hydrosulfite and advantageously with the aid of sodium hydrosulfite in the presence of sodium hydroxide or acetic acid, or with the aid of an alkaline sulfide and preferably with ammonium sulfide. Alternatively this reduction can be effected by catalytic hydrogenation of the indoaniline in the presence of a palladium on carbon catalyst.

According to a first advantageous method of reducing the indoaniline, excess sodium hydrosulfite is dissolved in a 1 N aqueous solution of NaOH. To the resulting solution there is added the benzoquinone-imine in solution in ethanol over a period of about 15–30 minutes, while stirring, and at a temperature between about 5°–30° C.

Stirring of the resulting mixture is continued until the solution becomes colorless, which generally requires between about 15–60 minutes. The aqueous solution is then cooled to 0° C by the addition of ice thereto and neutralized, preferably with acetic acid so as to precipitate the diphenylamine of the present invention in crystallized form. Certain diphenylamines precipitate when the said solution is cooled by the addition of solid carbon dioxide making unnecessary the neutralization procedures with acetic acid (see Example 6, infra.). When the benzoquinoneimine is difficulty soluble in ethanol, it is advantageous to dissolve the same in a 1:1 ethanol-dimethylformamide solution (see Example 14, infra).

The diphenylamines of Examples 2, 3, 5, 6, 9, 14–22 and 24–32, infra, have been prepared in accordance with this first embodiment outlined above.

The diphenylamines of Examples 1, 4, 7, 8, 10, 12, 13 and 23, infra, have been prepared according to a second embodiment according to which excess sodium hydrosulfite is dissolved in a 2–10 percent, preferably 3–5 percent aqueous acetic acid solution. To the resulting solution, maintained at a temperature between about 15° to 30° C, there is added, while agitating, the benzoquinoneimine in the form of a solution in ethanol. Agitation is continued until the solution becomes colorless, which generally requires between about 15 to 60 minutes. The solution is then neutralized by means of ammonia until the diphenylamine precipitates in crystallized form, this generally takes place at a pH of about 5 to 7.5.

According to a variation of this process (see Example 10, infra), sodium hydrosulfite is dissolved in a 5:1 water: ethanol solution.

The diphenylamines of the present invention are usefully employed for dyeing keratinic fibers and, in particular, living human hair.

The introduction of the above defined $R_6$ and $R_7$ groups not only enables variations in the solubility of the dye and its affinity for the keratinic fibers but it also increases the resistance of the dye to washing and to light.

The solubility of the diphenylamines of the present invention is further increased when, in accordance with formula (I), $R_6$ and $R_7$ represent hydroxyalkyl or sulfoalkyl. Further, the affinity of these diphenylamines for keratinic fibers in increased when $R_6$ or $R_7$ represents amino alkyl, piperidino alkyl or morpholino alkyl.

The diphenylamines of the present invention, when applied to hair in an aqueous or hydroalcoholic solution, at a concentration ranging between about 0.002 to 5 weight percent thereof, and preferably between 0.02 to 3 weight percent, provide, after oxidation either with air or by another oxidizing agent such as hydrogen peroxide, urea peroxide or ammonium persulfate, a range of shades which are very rich in the area of pinks to violets, blues and greens. Additionally, the diphenylamines of the present invention provide some very luminous grays and beiges which are rich in glints. The dyeings thus obtained are characterized by richness in glints and their pearly or metallic aspect.

The present invention also relates to a dye composition for keratinic fibers and in particular living human hair, comprising an aqueous or hydroalcoholic solution, and preferably hydroethanolic or hydroisopropanolic solution, containing at least one compound of the formula (I).

The dye composition can also include a salt of the diphenylamines of formula (I) and in particular the hydrochloride, hydrobromide, sulfate or phosphate thereof.

The dye compositions according to the present invention can include as the active dyeing agent only the compounds of formula (I). However, they can also include other known leuco derivatives of indoanilines, indamines or indophenols, or even oxidation dyes such as ortho- or para-phenylenediamines or ortho- or para-aminophenols, as well as benzene compounds trisubstituted by hydroxy, amino or alkoxy radicals and couplers such as metadiamines, metaaminophenols, metaacetylaminophenols, or even direct dyes such as nitrobenzene dyes, azo dyes or anthraquinone dyes, indoanilines, indamines and/or indophenols.

The compositions according to the present invention are generally provided in the form of an aqueous or hydroalcoholic solution containing one or more compounds of formula (I), in admixture or not with other dyes. They can, however, also include thickening agents and be provided in the form of a cream or gel.

Representative thickening agents that can be incorporated into the dye composition of the present invention include cellulose derivatives such as methyl cellulose, hydroxyethyl cellulose, carboxymethyl cellulose or acrylic polymers such as the sodium salt of polyacrylic acid or carboxyvinyl polymers.

The dye composition can contain as solvents, water, lower alkanols for example ethanol or isopropanol, polyalcohols such as glycols, for example, ethylene glycol, propylene glycol, butyl glycol, diethylene glycol and the monomethyl ether of diethylene glycol.

The dye composition according to the present invention can also include other components generally employed in cosmetics, such as surface active agents which can be used as carriers, as thickeners, as wetting agents or as dispersing agents; swelling agents; penetrating agents, emollients; polymers and/or perfumes. The composition of the present invention can also be packaged in aerosol containers together with an aerosol propellant.

Representative surface active agents which can be used include oxyethylenated alcohols and, in particular, oxyethylenated lauryl alcohol; oxyethylenated lauryl alcohol partially sulfated and preferably a mixture constituted by 19% lauryl alcohol oxyethylenated with 2 moles of ethylene oxide and 81% of the sodium sulfate salt of this same oxyethylenated alcohol; alkaline or ammonium sulfate salts of fatty alcohols having a long chain, for example ammonium lauryl sulfate; oxyethylenated alkylphenols and preferably nonylphenol oxyethylenated with 4 or 9 moles of ethylene oxide per mole of alkylphenol; oxyethylenated fatty acids; and sulfates and sulfonates of fatty alcohols optionally oxyethylenated.

Representative aerosol propellants usefully employed in compositions according to the present invention include nitrogen, nitrous oxide, volatile hydrocarbons such as butane, isobutane or propane, or preferably fluorinated hydrocarbons (sold under the name of Freon by Dupont) such as dichlorodifluoromethane, 1,1-difluoromethane, 1,2-dichloro-1,1,2,2-tetrafluoroethane and 1-chloro 1,1-difluoromethane. Mixtures of two or more hydrocarbons or fluorinated hydrocarbons can also be used.

The pH of the compositions of the present invention can vary widely and generally it ranges between about 5.5 to 12 and preferably between about 6.5 and 10.5.

The pH of the composition can be adjusted with the aid of an alkalizing agent such as, for example, ammonia, mono-, di- or tri-ethanolamine, di- or tri-sodium phosphate, sodium carbonate or potassium carbonate, or with the aid of an acidifying agent such as, for example, acetic acid, lactic acid, phosphoric acid or citric acid.

The dyeing of keratinic fibers and in particular living human hair, with the use of the dye compositions of the present invention is carried out in a conventional manner by applying the said composition to the fibers to be dyed, permitting said composition to remain in contact with the fibers for a period of time ranging from about 5 to 30 minutes, rinsing and optionally washing the fibers and then drying the fibers. Prior to applying the said composition to the fibers, there can be added to said composition an oxidizing agent such as 30–100 percent by volume of hydrogen peroxide, generally 6%, or 0.1 to 15% by weight of an oxidizing agent such as urea peroxide or ammonium persulfate.

The compositions according to the present invention, when present in the form of a hydroalcoholic solution, can also include a cosmetic resin, so as to provide a colored hair setting lotion which can be applied to wet hair before setting it in waves.

Representative cosmetic resins that can be used in the hair setting lotion compositions of the present invention include such film-forming polymers as polyvinylpyrrolidone; copolymers of vinylpyrrolidone and vinyl acetate; copolymers of vinyl acetate and an unsaturated carboxylic acid such as crotonic acid; copolymers resulting from the copolymerization of vinyl acetate, crotonic acid and an acrylic or methacrylic ester; copolymers resulting from the copolymerization of vinyl acetate and a vinyl alkyl ether; copolymers resulting from the copolymerization of vinyl acetate, crotonic acid and a vinyl ester of a long carbon chain acid or an allyl or methallyl ester of an acid with a long carbon chain, copolymers resulting from the copolymerization of an ester derived from an unsaturated alcohol and a short carbon chain acid, of an unsaturated short carbon chain acid and of at least one ester derived from a short carbon chain saturated alcohol and an unsaturated acid; and copolymers resulting from the copolymerization of at least one unsaturated ester and at least one unsaturated acid.

Representative preferred cosmetic resins include polyvinylpyrrolidone having a molecular weight ranging between about 10,000 to 360,000; copolymers of 10% crotonic acid and 90% vinyl acetate having a molecular weight ranging between about 10,000 to 70,000; copolymers of vinylpyrrolidone and vinyl acetate having a molecular weight ranging between about 30,000 to 200,000 wherein the ratio of VP to VA ranges between 30:70 to 70:30, copolymers of maleic anhydride and methylvinyl ether having a specific viscosity, measured at 25° C and at a concentration of 1g in 100 ml of methylethyl ketone, ranging between about 0.1 and 3.5; the ethyl, isopropyl and butyl monoesters of said maleic anhydride-methylvinyl ether copolymers; copolymers of maleic anhydride and vinylbutyl ether; terpolymers of methyl methacrylate (15-25%); stearyl methacrylate (25-35%) and dimethylaminoethyl methacrylate (52-62%), preferably quaternized, for example, by dimethyl sulfate, and the viscosity of which, measured at the boiling point of the ether and at a concentration of 5% in dimethylformamide, ranges between about 8-12 centipoises; terpolymers of vinyl acetate (75-85%), allyl stearate (10-20%) and allyloxyacetic acid (3-10%), the viscosity of which, measured at the boiling point of ether and at a concentration of 5% in dimethylformamide, ranges between about 4.4 and 5 centipoises.

These cosmetic film-forming resins are used generally in an amount between about 1–3 percent by weight of the total hair setting lotion composition.

The alcohols generally employed in the production of the hair setting lotion compositions of the present invention are low molecular weight alcohols, preferably ethanol or isopropanol. These alcohols are used in an amount of about 20–70 weight percent of said composition.

The hair setting lotion compositions of the present invention can be utilized in a conventional manner by applying the same to previously washed and rinsed wet or moist hair, followed by rolling the hair up on curlers and drying the hair.

The present invention is illustrated by the following non-limiting examples. These examples are tabulated in Tables I, I-bis, II, III and IV.

Examples of preparing the diphenylamines of the present invention appear in Tables I, I-bis and II. Table I, which indicates the characteristics of the prepared diphenylamines, has 9 columns numbered (1) through (9). Column (1) indicates the number of the example of preparation; the name of the compound prepared appears in column (2); columns (3) and (4) indicate, respectively, the melting point and the empirical formula, columns numbered (5) through (9) indicate, respectively, the percentages of C, H, N, Cl and S. For each compound prepared, columns (5) through (9) carry two to three lines, the first line indicating the theoretical percentages corresponding to the empirical formula of Col. (4), while the second and third lines indicate the percentages found by analysis.

Table I-bis indicates the characteristics of the benzoquinoneimines (indoanilines) which serve as an initial reactant in the preparation of the diphenylamines appearing in Table I. Table I-bis carries the same columns as Table I.

The benzoquinoneimines which do not appear in Table I-bis are described in Luxembourg Pat. No. 67,860, in Belgium Pat. No. 816,672 as well as in U.S. Application Ser. No. 482,523 filed June 24, 1974, now U.S. Pat. No. 3,944,629, all of which are incorporated herein by reference.

Table II, which indicates the manner in which the benzoquinoneimines appearing in Table I-bis are prepared, includes eight columns. Column (1) indicates, as in Table I, the number of the example of preparation. The columns following are numbered (11) through (17). Columns (11) and (12) indicate the name of the initial reactants, i.e. the substituted aniline in column (11) and substituted phenol in column (12). Column 13 entitled "ratio of (12):(11)" indicates the molar ratio between the substituted phenol and substituted aniline initial reactants.

Column (14) indicates the reaction medium, Column (15), the nature of the oxidizing agent used; Column (16) entitled "ratio of (15):(12)" indicates the molar ratio between the oxidizing agent and the substituted phenol; and Column (17) indicates the reaction temperature in centigrade degrees.

The examples of use include examples of simple dye compositions as well as dye compositions which also include a cosmetic resin and are called hair setting lotions. All examples of use are tubulated in Table III.

Table III carries 13 columns numbered (31) to (43). Column (31) indicates the number of the example of use. This column carries a number preceded by the letter A. Column (32) carries a figure which corresponds to a number appearing in column (1) of table I and indicates the diphenylamine used, or carries the letter C followed by a number which represents another dye used in admixture with the diphenylamine. The name of this latter dye appears at the bottom of the Table. Column (33) indicates the quantity of dye, expressed in percent by weight of the total weight of the composition. Columns (34) and (35) indicate, respectively, the nature and the weight percent of adjuvants used, based on the total weight of the simple dye composition or the hair setting lotion composition. In these columns appear the surface active agent, the thickening agent, the cosmetic polymer and all other components used in the dye composition and hair setting lotion composition.

Columns (36) and (37) indicate, respectively, the nature and the percent by weight of the total weight of the composition, of the solvent used other than water. The percent by weight of water used represents the difference between 100 g and the total weight appearing in columns (33), (35) and (37).

Columns (38), (39) and (40) indicate, respectively, the nature, the volume (expressed in ml) and the concentration of the solution of the oxidizing agent added to 100 g of the composition.

Column (41) indicates the pH of the composition while Column (43) indicates the color obtained on bleached hair (D) or on 95% naturally white hair (B 95), this latter indication appearing in Column (42).

In Columns (32), (34), (36) and (38), there appear the names, respectively, of dyes other than the diphenylamines of the present invention, the adjuvants which include the polymers the solvents and the oxidizing agents. These indications are given by abbreviations, for which the meanings, and in the case of the polymers, such characteristics as molecular weight or viscosity, appear at the bottom of the Tables. Unless indicated to the contrary, all percentages are by weight of the total weight of the dye composition or the hair setting lotion composition.

TABLE I

| Ex. No. (1) | DIPHENYLAMINE (2) | M.P. (° C) (3) | Empirical Formula (4) | ANALYSIS C % (5) | H % (6) | N % (7) | Cl % (8) | S % (9) |
|---|---|---|---|---|---|---|---|---|
| 1 | 3-methyl-4-hydroxy-6-carbamylmethyl-amino-4'-N,N-(di-β-hydroxyethyl) amino diphenylamine | 212 | $C_{19}H_{26}N_4O_4$ | 60.94 / 60.76 / 60.80 | 7.00 / 6.85 / 6.92 | 14.96 / 15.08 / 15.06 | | |
| 2 | 3,5-dimethyl-2-acetylamino-4-hydroxy-4'-N,N(ethyl, carbamylmethyl)amino diphenylamine | 140 | $C_{20}H_{26}N_4O_3$ MW 370 (a) MW 367 (b) | 64.84 / 63.75 / 63.82 | 7.07 / 7.09 / 7.10 | 15.13 / 15.02 / 15.10 | | |
| 3 | 3,2'-dimethyl 4-hydroxy 6-acetyl-amino 4'-N,N-(ethyl,carbamylmethyl) amino diphenylamine | 202 | $C_{20}H_{26}N_4O_3$ MW 370 (a) MW 366 (b) | 64.84 / 64.69 | 7.07 / 6.91 | 15.13 / 15.34 | | |
| 4 | 3,5-dimethyl-2-amino-4-hydroxy-2'-chloro 4'-N,N-(di-β-hydroxyethyl) amino diphenylamine, semi-hydrate | 100 | $C_{18}H_{24}N_3O_3Cl \cdot 0.5 H_2O$ | 57.60 / 57.76 / 57.65 | 7.00 / 6.95 / 6.87 | 11.20 / 11.20 / 11.38 | 9.45 / 9.24 / 9.43 | |
| 5 | 3-methyl-4-hydroxy-6-amino-4'-N-(di-β-hydroxyethyl)amino diphenyl-amine | 135 | $C_{17}H_{23}N_3O_3$ MW 317 (a) MW 317 (b) | 64.33 / 64.13 | 7.30 / 7.46 | 13.24 / 13.16 | | |
| 6 | 3,5-dimethyl-2-acetylamino-4-hydroxy-4'-N,N-(di-β-hydroxyethyl) amino diphenylamine | 153 | $C_{20}H_{27}N_3O_4$ MW 373 (a) MW 378 (b) | 64.32 / 63.97 / 64.12 | 7.29 / 7.30 / 7.44 | 11.25 / 11.37 / 11.45 | | |
| 7 | Monohydrate of 2-ureido-4-hydroxy-2'-methyl-4'-N,N(ethyl, carbamylmethyl)amino diphenylamine (a) Calculated molecular weight (b) Molecular weight found by potentiometric titration in acetic acid with the use of perchloric acid | 126 | $C_{18}H_{25}N_5O_4$ | 57.60 / 57.21 / 57.12 | 6.66 / 6.63 / 6.55 | 18.66 / 18.76 / 18.62 | | |
| 8 | 2-acetylamino-3,5,2'-trimethyl-4-hydroxy-4'-N,N-(ethyl, β-mesylamino-ethyl) amino diphenylamine | 100–102 | $C_{22}H_{32}N_4O_4S$ | 58.91 / 58.52 / 58.68 | 7.19 / 6.89 / 6.96 | 12.49 / 12.37 / 12.41 | | |
| 9 | Monohydrate of 2-chloro-4-hydroxy-5-acetylamino-4'-N,N-(ethyl, β-piperidinoethyl)amino diphenylamine, dihydrochloride | 181 with decomposition | $C_{23}H_{35}N_4O_3Cl_3$ | 52.92 / 53.05 / 53.11 | 6.71 / 6.56 / 6.61 | 10.73 / 10.82 / 10.71 | 20.42 / 20.69 / 20.74 | |
| 10 | 3,5-dimethyl-2-amino-4-hydroxy-2'-methoxy-4'-N,N-(di-β-hydroxyethyl)-amino diphenylamine | 140 | $C_{19}H_{27}N_3O_4$ MW 361 (a) MW 367 (b) | 63.14 / 62.87 / 62.94 | 7.53 / 7.56 / 7.41 | 11.63 / 11.89 / 11.96 | | |
| 11 | 3,5-dimethyl-2-amino-4-hydroxy-4'-N,N-(ethyl, carbamylmethyl)amino diphenylamine | 168 | $C_{18}H_{24}N_4O_2$ | 65.83 / 65.91 / 65.67 | 7.37 / 7.46 / 7.53 | 17.06 / 16.92 / 16.96 | | |
| 12 | 3-methyl-6-acetylamino-4-hydroxy-4'-N,N-(di-β-hydroxyethyl)amino diphenylamine | 179 | $C_{19}H_{25}N_3O_4$ | 63.49 / 63.00 / 62.96 | 7.01 / 7.05 / 7.12 | 11.69 / 11.98 / 11.87 | | |
| 13 | 3,5-dimethyl-2-amino-4-hydroxy-4'-N,N-(di-β-hydroxyethyl)amino diphenylamine | 128 | $C_{18}H_{25}N_3O_3$ | 65.23 / 64.67 / 64.76 | 7.60 / 7.52 / 7.47 | 12.68 / 12.74 / 12.82 | | |
| 14 | 3,5,2'-trimethyl-2-amino 4-hydroxy-4'-N,N-(ethyl,β-benzoylaminoethyl) amino diphenylamine | 117 | $C_{26}H_{32}N_4O_2$ | 72.19 / 71.96 / 71.84 | 7.46 / 7.31 / 7.29 | 12.95 / 12.79 / 12.82 | | |
| 15 | 3,5-dimethyl-2-amino-4-hydroxy-4'-N,N-(ethyl,β-sulfoethyl)amino diphenylamine monohydrate | 230 | $C_{18}H_{25}N_3O_4S \cdot H_2O$ | 54.40 / 54.39 / 54.45 | 6.80 / 6.92 / 7.05 | 10.57 / 10.58 / 10.76 | | 8.06 / 8.22 / 8.17 |
| 16 | 3,5,2'-trimethyl-2-amino-4-hydroxy-4'-N,N-(ethyl,β-acetylaminoethyl) amino diphenylamine monohydrate | 90 | $C_{21}H_{30}N_4O_2 \cdot H_2O$ | 65.00 / 65.37 / 65.37 | 8.25 / 7.95 / 8.17 | 14.45 / 14.66 / 14.66 | | |
| 17 | 3-methoxy-4-hydroxy-6-acetylamino-4'-N,N-(ethyl, carbamylmethyl) amino diphenylamine | 228 | $C_{19}H_{24}N_4O_4$ | 61.29 / 61.30 | 6.45 / 6.71 | 15.05 / 14.97 | | |
| 18 | 3-chloro-4-hydroxy-6-acetylamino-4'-N,N-(ethyl, carbamylmethyl) amino diphenylamine | 270 | $C_{18}H_{21}N_4O_3Cl$ | 57.37 / 57.23 | 5.67 / 5.90 | 14.87 / 14.64 | | |
| 19 | 3-methyl-4-hydroxy-6-β-hydroxy-ethylamino-4'-N,N-(ethyl, carbamyl-methyl)amino diphenylamine mono-hydrate | 142 | $C_{19}H_{26}N_4O_3 \cdot H_2O$ | 60.62 / 60.44 | 7.50 / 7.45 | 14.88 / 14.65 | | |
| 20 | 3-methyl-6-carbethoxyamino-4-hydroxy 4'-N,N-(ethyl, carbamylmethyl) amino diphenylamine | 168 | $C_{20}H_{26}N_4O_4$ | 62.16 / 62.35 | 6.78 / 6.50 | 14.50 / 14.27 | | |
| 21 | 2-methoxy-4-hydroxy-4'-N,N-(ethyl, carbamylmethyl) amino diphenylamine | 155 | $C_{17}H_{21}N_3O_3$ | 64.76 / 64.52 | 6.66 / 6.68 | 13.33 / 13.45 | | |
| 22 | 3,6,2'-trimethyl-4-hydroxy-4'-N,N-(ethyl, mesylaminoethyl) amino diphenylamine | 90 | $C_{20}H_{29}N_3SO_3$ | 61.36 / 61.41 | 7.47 / 7.25 | 10.74 / 10.48 | 8.17 | 8.36 |
| 23 | 3,5-dimethyl-2-acetylamino-4-hydroxy-4'-N,N-(ethyl,β-mesylamino-ethyl) amino diphenylamine | 110 | $C_{21}H_{30}N_4O_4S$ | | | 12.90 / 12.77 / 12.70 | | 7.36 / 7.56 / 7.52 |
| 24 | 3-methyl-4-hydroxy-6-carbamylmethyl-amino-4'-N,N-(ethyl, β-mesylamino-ethyl) amino diphenylamine | 197 | $C_{20}H_{29}N_5O_4S$ | 55.16 / 55.18 | 6.71 / 6.62 | 16.08 / 15.80 | | 7.35 / 7.35 |
| 25 | 3,2'-dimethyl-4-hydroxy-6-carbamyl-methylamino-4'-N,N-(ethyl, β-mesyl-aminoethyl) amino diphenylamine | 144 | $C_{21}H_{31}N_5O_4S$ | 56.11 / 55.98 | 6.95 / 6.85 | 15.58 / 15.37 | | 7.12 / 7.25 |
| 26 | 3-methyl-4-hydroxy-6-acetylamino-2'-methyl-4'-N,N-(ethyl-β-mesyl-aminoethyl) amino diphenylamine | 169 | $C_{21}H_{30}N_4O_4S$ | | | 12.90 / 13.20 | | 7.37 / 7.56 |
| 27 | 3-methyl-4-hydroxy-6-ureido-4'-N,N-(di-β-hydroxyethyl) amino diphenyl-amine | 201 | $C_{18}H_{24}N_4O_4$ | 60.00 / 59.95 | 6.66 / 6.88 | 15.55 / 15.34 | | |

TABLE I-continued

| Ex. No. (1) | DIPHENYLAMINE (2) | M.P. (° C) (3) | Empirical Formula (4) | ANALYSIS | | | | |
|---|---|---|---|---|---|---|---|---|
| | | | | C % (5) | H % (6) | N % (7) | Cl % (8) | S % (9) |
| 28 | 3-methyl-4-hydroxy-6-ureido-4'-N,N-(ethyl,carbamylmethyl) amino-2'-methyl diphenylamine | 240 | $C_{19}H_{25}N_5O_3$ | 61.45 61.28 61.17 | 6.74 6.69 6.58 | 18.86 19.00 19.10 | | |
| 29 | 3,5-dimethyl-4-hydroxy-4'-N,N-(ethyl, carbamylmethyl) amino diphenylamine | 151 | $C_{18}H_{23}N_3O_2$ | 68.98 68.84 | 7.40 7.47 | 13.41 13.49 | | |
| 30 | 3-methyl-4-hydroxy-6-acetylamino-4'-N,N-(ethyl, carbamylmethyl) amino diphenylamine | 265 | $C_{19}H_{24}N_4O_3$ | 64.04 63.92 63.89 | 6.74 6.63 6.58 | 15.73 15.95 15.93 | | |
| 31 | 3-methyl-4-hydroxy-6-amino-4'-N,N-(ethyl, carbamylmethyl) amino diphenylamine monohydrate | 142 | $C_{17}H_{22}N_4O_2 \cdot H_2O$ | 61.44 61.68 | 7.22 7.20 | 16.87 16.88 | | |
| 32 | 3-methyl-4-hydroxy-6-carbamylmethyl-amino-4'-N,N-(ethyl, carbamylmethyl) amino diphenylamine semi-hydrate | 250 | $C_{19}H_{25}N_5O_3 \cdot 0.5 H_2O$ | 60.00 59.87 | 6.84 6.75 | 18.42 18.35 | | |

TABLE I-Bis

| EX. No. (1) | BENZOQUINONEIMINE (2) | M.P. (3) | Empirical Formula (4) | C% (5) | H% (6) | N% (7) | Cl% (8) | S% (9) |
|---|---|---|---|---|---|---|---|---|
| 1 | N-[(4'-(di-β-hydroxyethyl)amino) phenyl]-2-methyl-5-carbamylmethyl-amino benzoquinone imine | 205 | $C_{19}H_{24}N_4O_4$ | 61.29 61.02 60.98 | 6.45 6.57 6.62 | 15.05 15.27 15.31 | | |
| 2 | N-[(4'-(ethyl, carbamylmethyl) amino) phenyl]-2,6-dimethyl-3-acetylamino benzoquinoneimine | 222 | $C_{20}H_{24}N_4O_3$ | 65.22 65.22 65.26 | 6.52 6.78 6.75 | 15.22 15.10 15.19 | | |
| 17 | N-[(4'-(ethyl, carbamylmethyl) amino) phenyl]-2-methoxy-5-acetyl-amino benzoquinoneimine monohydrate | 258 | $C_{19}H_{22}N_4O_4 \cdot H_2O$ | 58.76 58.61 | 6.19 6.29 | 14.43 14.49 | | |
| 18 | N-[(4'-(ethyl, carbamylmethyl) amino) phenyl]-2-chloro-5-acetyl-amino benzoquinoneimine | 215 | $C_{18}H_{19}N_4O_3Cl$ | | | 14.26 14.00 | 9.04 8.78 | |
| 19 | N-[(4'-ethyl, carbamylmethyl) amino) phenyl]-2-methyl-5-β-hydroxy-ethylamino benzoquinoneimine | 170 | $C_{19}H_{24}N_4O_3$ | 64.04 63.99 | 6.74 6.52 | 15.73 15.50 | | |
| 21 | N-[(4'-(ethyl, carbamylmethyl) amino) phenyl]-3-methoxy benzo-quinoneimine | 232 | $C_{17}H_{19}N_3O_3$ | 65.17 64.88 | 6.07 6.09 | 13.42 13.49 | | |
| 25 | N[(4'-(ethyl, mesylaminoethyl) amino)-2'-methyl) phenyl]-2-methyl-5-carbamylmethylamino benzoquinone-imine monohydrate | 196 | $C_{21}H_{29}N_3O_4S \cdot H_2O$ | 54.2 54.09 53.79 | 6.6 6.54 6.53 | 15.0 14.81 14.89 | | 6.88 7.10 7.13 |
| 31 | N-[(4'-(ethyl, carbamylmethyl) amino) phenyl]-2-methyl-5-amino benzoquinoneimine | 210 | $C_{17}H_{20}N_4O_2$ | 65.38 65.49 | 6.41 6.48 | 17.97 17.82 | | |
| 32 | N-[(4'-(ethyl, carbamylmethyl) amino) phenyl]-2-methyl-5-carbamylmethyl-amino benzoquinoneimine | 222 | $C_{19}H_{23}N_5O_3$ | 61.77 61.43 61.52 | 6.28 6.42 6.40 | 18.96 19.27 19.21 | | |

TABLE II

PREPARATION OF STARTING BENZOQUINONEIMINES

| Ex. No. | SUBSTITUTED ANILINE (11) | PHENOL Substituted Phenol (12) | Ratio of (12):(11) (13) | Reaction Medium (14) | Oxidizing Agent (15) | Ratio of (15):(12) (16) | Temperature ° C (17) |
|---|---|---|---|---|---|---|---|
| 1 | 4-nitroso-N,N-(di-β-hydroxy-ethyl) aniline hydrochloride | 2-methyl-5-carbamyl-methyl-amino phenol | 1:1.1 | Ethanol-water 1:1 | | | 50° |
| 2 | 4-amino-N,N-(ethyl, carbamylmethyl) aniline | 2,6-dimethyl-3-acetylamino phenol | 1:1.1 | Isopropa-water 1:3 | Ammonium Persulfate | 2.2:1 | 0° |
| 17 | " | 2-methoxy-5-acetyl-amino phenol | 1:1 | acetone-water 1:2 | " | 2:1 | 0° |
| 18 | " | 2-chloro-5-acetyl-amino phenol | 1:1 | acetone-water 1:1 | " | 2:1 | 0° |
| 19 | " | 2-methyl-5-β-hydroxyethylamino phenol | 1:1 | " | " | 1:1 | 5° |
| 21 | " | 3-methoxy phenol | 1:1 | Isopropa-nol-water 1:2 | " | 2:1 | 0–5° |
| 25 | 4-amino-3-methyl-N,N-(ethylmesylaminoethyl) aniline dihydrochloride | 2-methyl-5-carbamyl-methylamino phenol | 1:1 | acetone-water 1:1.5 | " | 2:1 | 0–5° |
| 31 | 4-amino-N,N-(ethyl, carbamylmethyl) aniline | 2-methyl-5-amino phenol | 1:1 | acetone-water 1:1 | " | 2:1 | 0 |
| 32 | " | 2-methyl-5-carbamyl-methylamino phenol | 1:1 | acetone-water 1:1 | " | 2:1 | 0 |

TABLE III

| (31) EX. No. | (32) DYE EX. No. | (33) % | (34) ADJUVANT Nature | (35) % | (36) SOLVENT Nature | (37) % | (38) Oxidizing Agent Nature | (39) ml | (40) conc. | (41) pH | (42) Hair | (43) Color |
|---|---|---|---|---|---|---|---|---|---|---|---|---|
| A 1 | 3 | 0.02 | AL 10.5 OE (1) | 5 | | | PSA (9A) | 100 | 0.02% | 6.5 | D (4) | horizon blue |
| A 2 | 5 | 0.2 | | | Ethanol | 30 | H₂O₂ | 40 | 6% | 10.5 | " | mauve |
| A 3 | 12 | 0.16 | DC (2) | 10 | | | PU (9B) | 100 | 10% | 10 | " | royal blue |
| A 4 | 11 | 0.49 | AL 10.5 OE (1) | 20 | | | H₂O₂(9C) | 100 | 6% | 9 | " | pearly pink mauve |
| A 5 | 15 | 0.5 | AcP (3) | 4.7 | | | H₂O₂ | 50 | 6% | 9 | B95 (5) | raw pink |
| A 6 | 9 | 0.57 | LSS 19 (6) EDTA (7) 40% NaHSO₃ solution | 20 0.2 1 | | | | | | 11.3 | " | verbena with golden glints |
| A 7 | 13 | 3.05 | CMC (11bis) | 7 | Ethanol | 30 | | | | 8 | " | gray with mauve glints |
| A 8 | 7 | 1.98 | | | | | H₂O₂ | 100 | 6% | 10 | " | pearly pale blue-green |
| A 9 | 1 | 1.07 | AL 10.5 OE (1) | 5 | Butylglycol | 5 | | | | 8.15 | D | silvery grey with mauve glints |
| A 10 | 2 | 0.15 | LSS 19 (6) | 20 | | | | | | 8.5 | B95 | hazel with pink glints |
| | C1 (8) | 0.10 | EDTA (7) | 0.2 | | | | | | | | |
| | C2 (9) | 0.4 | | | | | | | | | | |
| | C3 (10) | 0.2 | | | | | | | | | | |
| | C4 (11) | 1 | | | | | | | | | | |
| A 11 | 12 | 0.07 | | | Ethanol | 30 | H₂O₂ | 30 | 6% | 10.5 | D | maroon with light violet glints |
| | C5 (12) | 0.13 | | | | | | | | | | |
| | C2 (9) | 0.25 | | | | | | | | | | |
| | C4 (11) | 0.45 | | | | | | | | | | |
| | C6 (13) | 0.15 | | | | | | | | | | |
| A 12 | 3 | 0.50 | LSS 19 (6) | 20 | | | | | | 10 | B 95 | Very luminous yellow green |
| A 12 | C7 (14) | 0.3 | EDTA (7) | 0.2 | | | | | | | | |
| | C8 (15) | 0.08 | | | | | | | | | | |
| | C9 (16) | 0.08 | | | | | | | | | | |
| A 13 | 8 | 2 | | | Ethanol | 45 | | | | 10.8 | B 95 | marine algae |
| A 14 | 2 | 0.5 | R—(O—CH₂—CH)₂OH<br>                       CH₂OH<br>R = oleyl<br>R—(O—CH₂—CH)₄OH<br>                       CH₂OH<br>R = oleyl | 4<br><br><br><br>5 | propylene glycol | 7.4 | H₂O₂ | 100 | 6% | 10.5 | B 95 | tin gray |
| A 15 | 5 | 0.12 | LSS 19 (6) EDTA (7) | 20 0.2 | | | | | | 9.9 | D | mauve |
| A 16 | 3 | 0.16 | LSA (17) | 7.7 | Isopropanol | 23 | H₂O₂ | 30 | 6% | 8 | D | pearly light blue |
| A 17 | 6 | 0.38 | LSA (17) | 10 | | | | | | 8.6 | B 95 | pearly pale green with golden glints |
| A 18 | 5 | 0.1 | AL 10.5 OE (1) | 5 | Butylglycol | 5 | H₂O₂ | 100 | 6% | 9 | B95 | cognac |
| | C10 (18) | 2 | | | | | | | | | | |
| A 19 | 3 | 0.2 | D C (2) | 10 | | | H₂O₂ | 50 | 6% | 10 | B95 | ash beige with violet glints |
| | C11 (19) | 0.3 | | | | | | | | | | |
| A 20 | 6 | 0.40 | PVP (23) MW = 40,000 | 2 | Isopropanol | 25 | | | | 9.5 | D | light golden chestnut |
| | C12 (20) | 0.20 | | | | | | | | | | |
| | C13 (21) | 0.25 | | | | | | | | | | |
| | C14 (22) | 0.08 | | | | | | | | | | |
| A 21 | 14 | 0.50 | VA/CA (24) MW = 50,000 | 2 | Ethanol | 50 | | | | 8 | B95 | metallic gray with violet glints |
| A 22 | 16 | 0.75 | VA/CA (24) MW = 10,000 | 2 | Ethanol | 50 | | | | 9.5 | B95 | beige gray with pink glints |
| A 23 | 6 | 1.52 | VP/VA 60/40 (25) | 2 | Isopropanol | 35 | | | | 7.2 | D | royal blue |
| A 24 | 11 | 0.19 | VP/VA 30/70 (26) | 2 | Ethanol | 40 | | | | 6 | D | lightly mauvish pink |
| A 25 | 16 | 0.15 | | | | | | | | | | |
| | 9 | 0.28 | | | | | | | | | | |
| | C15 (27) | 0.05 | | | | | | | | | | |
| | C 9 (16) | 0.10 | VP/VA 70/30 (28) | 3 | Isopropanol | 35 | | | | 11 | D | violine |
| A 26 | 10 | 0.4 | VA/CA (24) MW 50,000 | 2 | Ethanol | 50 | | | | 7 | D | luminous mauve |
| A 27 | 4 | 0.1 | MM/StM/DM (29) | 2.5 | Ethanol | 30 | | | | 8.5 | D | golden pink with mauve glints |
| A 28 | 26 | 1.5 | | | Ethanol<br>E M D G (30) | 20<br>8 | | | | 5 | D | royal blue |
| A 29 | 24 | 0.75 | LSS 19 (6) | 20 | | | | | | 10.5 | | |

TABLE III-continued

| (31) EX. No. | (32) DYE EX. No. | (33) % | (34) ADJUVANT Nature | (35) % | (36) SOLVENT Nature | (37) % | (38) Oxidizing Agent Nature | (39) ml | (40) conc. | (41) pH | (42) Hair | (43) Color |
|---|---|---|---|---|---|---|---|---|---|---|---|---|
| | | | EDTA (7) | 0.2 | | | PU(9B) | 20 | 10% | | D | light blond with mauve glints |
| A 30 | 30 | 2 | LSS 19 (6) EDTA (7) | 20 0.2 | | | | | | 10.8 | D | bluish silver light-blond |
| A 31 | 28 | 1.5 | DC (2) | 8 | Ethanol | 20 | $H_2O_2$ | 40 | 6% | 11 | D | silvery myosotis |
| A 32 | 20 | 0.6 | VA/CA (24) MW = 50,000 | 1 | Ethanol | 36 | | | | 5 | D | glycine |
| A 33 | 27 | 0.4 | PVP (23) MW = 40,000 | 2 | Isopropanol | 25 | | | | 5.5 | D | deep pure blue |
| A 34 | 29 | 0.35 | VP/VA 60/40 (25) | 2 | Isopropanol | 35 | | | | 4.5 | D | deep mauve |
| A 35 | 25 | 0.4 | VA/CA (24) MW = 50,000 | 1 | Ethanol | 36 | | | | 5 | B95 | metallic mauve gray |
| A 36 | 31 | 0.5 | VP/VA 70/30 (31) | 3 | Ethanol | 25 | | | | 9 | D | deep purple |
| A 37 | 32 | 0.5 | VP/VA 30/70 (26) | 3 | Ethanol | 40 | | | | 9 | D | tamarisk pink |
| A 38 | 17 | 0.6 | PVP (23) MW = 360,000 | 2 | Isopropanol | 35 | | | | 9 | D | silvery mauve gray |
| A 39 | 23 | 0.3 | "Gafquat 734" (32) | 2 | Isopropanol | 20 | | | | 5 | D | silvery light blue |
| A 40 | 19 | 0.5 | "Gafquat 734"(32) | 2 | Isopropanol | 20 | | | | 8 | D | parme |
| A 41 | 22 | 0.4 | VA/AS/AA (33) | 2.5 | Ethanol | 50 | | | | 9.5 | D | pure blue |
| A 42 | 21 | 0.5 | VA/AS/AA (33) | 2.5 | Ethanol | 50 | | | | 7.5 | D | very silvery mauve gray |
| A 43 | 18 | 0.4 | MA-MVE/BE (34) | 1 | Ethanol | 45 | | | | 10 | D | pearly pale green |

(1) AL 1.5 OE = Lauryl alcohol oxyethylenated with 10.5 moles of ethylene oxide
(2) DC = Diethanolamides of fatty acids of coprah
(3) AcP = Acrylic acid polymer, MW = 2-3 million
(4) D = Bleached hair
(5) B 95 = 95% naturally white hair
(6) LSS 19 = Mixture comprising 19% lauryl alcohol oxyethylenated with 2 moles ethylene oxide and 81% of the sodium sulfate salt of this same oxyethylenated alcohol
(7) EDTA = Ethylenediamine tetraacetic acid
(8) C1 = 3-methyl-4-hydroxy-6-carbamylmethylamino-4'-N,N-dibutylamino diphenylamine
(9) C2 = 2,4-diaminoanisole
(9A) PSA = Ammonium persulfate
(9B) PU = Urea peroxide
(9C) $H_2O_2$ = Hydrogen peroxide
(10) C3 = Metaaminophenol
(11) C4 = Paraaminophenol
(11bis) CMC = Carboxymethylcellulose.
(12) C5 = 2-acetylamino-4-hydroxy-4'-N,N-dimethylamino diphenylamine
(13) C6 = Resorcin
(14) C7 = 4-hydroxy-3-methyl-6-ureido-4'-N,N-dimethylamino diphenylamine
(15) C8 = Nitro-metaphenylene diamine
(16) C9 = 1-γ-aminopropylamino anthraquinone
(17) LSA = Ammonium lauryl sulfate.
(18) C10 = 2-amino-4-methoxy phenol
(19) C11 = N-[4'(hydroxy) phenyl]-2-methoxy-5-amino benzoquinone diimine
(20) C12 = 1-N,N-(di-β-hydroxyethyl)amino-3-nitro-4-N'-methylaminobenzene
(21) C13 = 3-methyl-4,4'-dihydroxy-6-amino diphenylamine
(22) C14 = nitro-orthophenylenediamine
(23) PVP = Polyvinylpyrrolidone
(24) VA/CA = Copolymer of vinyl acetate and crotonic acid 90:10
(25) VP/VA 60/40 = Copolymer of vinylpyrrolidone and vinyl acetate 60/40 having a viscosity of 3.3 to 4 centipoises at 25° C in a 5% solution in ethanol
(26) VP/VA 30/70 = Copolymer of vinylpyrrolidone vinyl acetate 30/70 MW = 160,000
(27) C15 = Nitro-paraphenylenediamine
(28) VP/VA 70/30 = Copolymer of vinylpyrrolidone/vinyl acetate 70/30 MW = 40,000
(29) MM/StM/DM = Terpolymer of methyl methacrylate (15-25%)-stearyl methacrylate 25/35)-dimethylaminoethyl methacrylate (52-62%) quaternized with dimethyl sulfate.
(30) EMDG = monomethyl ether of diethylene glycol
(31) Copolymer of vinylpyrrolidone/vinyl acetate, 70/30 having an average molecular weight of 40,000.
(32) Quaternized copolymer of polypyrrolidone having a molecular weight in the order of 100,000 and sold under the trade mark "Gafquat 734" by General Aniline and Film Corporation
(33) VA/AS/AA = Terpolymer of vinyl acetate (80.5%) allyl stearate (15%) and allyloxyacetic acid (4.5%)
(34) Monobutylester of the copolymer of maleic anhydride and methyl vinylether having a specific viscosity of 0.1-0.5 measured at 25° C at a concentration of 1% in methylethylketone and sold under the trademark "GANTEZ ES 435" by General Aniline & Film Corp.

What is claimed is:

1. A composition for coloring keratinic fibers comprising an aqueous or hydroalcoholic solution of a diphenylamine of the formula

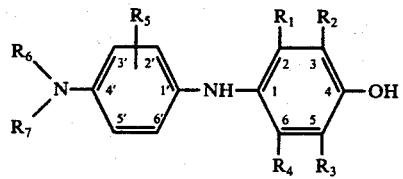

wherein
$R_1$ and $R_4$ each independently represent a member selected from the group consisting of hydrogen, halogen, lower alkyl, lower alkoxy, amino, lower alkylamino, acetylamino, lower carbamylalkylamino, lower hydroxyalkyl amino, lower carbalkoxy amino and ureido;

$R_2$ and $R_3$ each independently represent a member selected from the group consisting of hydrogen, halogen, lower alkyl, lower alkoxy, acetylamino and ureido;

$R_5$ represents a member selected from the group consisting of hydrogen, halogen, lower alkyl and lower alkoxy;

$R_6$ represents a member selected from the group consisting of lower hydroxyalkyl, lower acylamino alkyl, lower mesylamino alkyl, lower carbamylalkyl, lower sulfoalkyl and lower piperidinoalkyl, ; and $R_7$ represents a member selected from the group consisting of lower alkyl, lower hydroxyalkyl, lower acylamino alkyl, lower mesylamino alkyl, lower carbamyl alkyl, lower sulfoalkyl and lower piperidinoalkyl, each of said alkyl and alkoxy moieties containing 1–6 carbon atoms and each of said acyl moieties representing R—CO— wherein R is selected from the group consisting of an aliphatic and aromatic group, said composition having a pH between 5–12 and said diphenylamine being present in an amount of about 0.002 to 5 percent by weight of said composition.

2. The composition of claim 1 which also includes a direct hair dye.

3. The composition of claim 1 which also includes a member selected from the group consisting of an oxidation base and a coupler.

4. The composition of claim 3 wherein said oxidation base is selected from the group consisting of orthophenylenediamine, paraphenylenediamine, orthoaminophenol and paraaminophenol.

5. The composition of claim 3 wherein said coupler is selected from the group consisting of metadiamine, metaaminophenol, metaacetylamino phenol and metadiphenol.

6. The composition of claim 1 which also includes another diphenylamine.

7. The composition of claim 6 wherein said another diphenylamine is a leuco-indophenol.

8. The composition of claim 1 which also includes a dye selected from the group consisting of a nitrobenzene dye, an anthraquinone dye, an indamine and an indoaniline.

9. The composition of claim 1 which includes in said hydroalcoholic solution at least one cosmetic film-forming resin.

10. The composition of claim 9 wherein said hydroalcoholic solution is an aqueous solution of a low molecular weight alcohol.

11. The composition of claim 10 wherein said alcohol is selected from the group consisting of ethanol and isopropanol.

12. The composition of claim 10 wherein said alcohol is present in an amount of about 20–70 weight percent.

13. The composition of claim 9 wherein said cosmetic film-forming resin is present in an amount of 1–3 weight percent.

14. The composition of claim 9 wherein said cosmetic film-forming resin is selected from the group consisting of polyvinylpyrrolidone, a copolymer of vinylpyrrolidone and vinyl acetate, a copolymer of vinyl acetate and crotonic acid, a copolymer of maleic anhydride and butyl vinyl ether, a terpolymer of methyl methacrylate stearyl methacrylate and dimethylaminoethyl methacrylate quaternized by dimethyl sulfate and a terpolymer of vinyl acetate, allyl acetate and allyloxy acetic acid.

15. The composition of claim 1 which also includes an oxidizing agent.

16. The composition of claim 15 wherein said oxidizing agent is selected from the group consisting of hydrogen peroxide, ammonium persulfate and urea peroxide.

17. A process for dyeing keratinic fibers comprising impregnating said fibers to be dyed with an effective amount of the composition of claim 1, permitting said composition to remain in contact with said fibers for a period ranging from about 5 to 30 minutes, rinsing said fibers and drying said fibers.

18. The process of claim 17 wherein said fibers are living human hair and said hair after rinsing is shampooed prior to drying the same.

19. A process for coloring human hair comprising applying to previously washed and rinsed hair an effective amount of the composition of claim 9, rolling the hair on curlers and drying the hair.

* * * * *